United States Patent [19]

Konopka et al.

[11] Patent Number: 4,793,486
[45] Date of Patent: Dec. 27, 1988

[54] PROTECTIVE BAG FOR WATER-SENSITIVE MEDICAL OR ELECTRONIC APPARATUS

[75] Inventors: April A. Konopka, San Dimas; John H. Livingston, Santa Monica, both of Calif.

[73] Assignee: Pacesetter Infusion, Ltd., Sylmar, Calif.

[21] Appl. No.: 873,237

[22] Filed: Jun. 11, 1986

[51] Int. Cl.⁴ .................. A61B 19/02; B65D 85/38; B65D 30/10; B31B 1/76

[52] U.S. Cl. .................. 206/438; 4/604; 206/305; 206/806; 224/205; 383/8; 383/24; 383/95; 383/99; 383/106; 383/108; 493/243; 493/264; 604/151; 604/174

[58] Field of Search .......... 206/438, 439, 811, 806, 206/305; 383/98, 99, 93, 95, 42, 61, 87, 24, 106–108, 30, 31, 21, 22, 8; 493/243, 264; 4/604; 224/202, 205; 229/485 B; 604/151, 174; 2/49 R, 49 A, 52

[56] References Cited

U.S. PATENT DOCUMENTS

| | | | |
|---|---|---|---|
| 1,823,155 | 9/1931 | McArdle | 383/108 |
| 2,993,313 | 7/1961 | Hogan | 383/9 |
| 3,042,796 | 7/1962 | DeForest | 206/811 X |
| 3,070,278 | 12/1962 | Korn | 383/9 X |
| 3,197,073 | 7/1965 | Gondra et al. | 383/904 X |
| 3,279,331 | 10/1966 | Platt | 383/86 X |
| 3,488,275 | 1/1970 | Loyd | 206/525 X |
| 4,069,955 | 1/1978 | Noyes | 224/205 |
| 4,087,864 | 5/1978 | LaBove et al. | 604/174 X |
| 4,186,443 | 2/1980 | Britzman | 2/49 R |
| 4,276,982 | 7/1981 | Sibrava | 206/439 |
| 4,347,956 | 9/1982 | Berger | 224/202 |

FOREIGN PATENT DOCUMENTS

| | | | |
|---|---|---|---|
| 0263621 | 7/1968 | Austria | 383/7 |
| 469661 | 7/1937 | United Kingdom | 229/92 |

OTHER PUBLICATIONS

Enlarged Figure 11 of Platt.

*Primary Examiner*—Stephen Marcus
*Assistant Examiner*—Bryon Gehman
*Attorney, Agent, or Firm*—Leslie S. Miller

[57] ABSTRACT

An enclosure for use to safely secure a water-sensitive medical or electronic device such as a medication infusion pump in a water-resistant manner is disclosed which utilizes a pouch made of a sheet of thin plastic material to store the apparatus, the pouch being adhesively sealable to secure the device. The enclosure also includes a perforated area which may be opened to form a strap to carry or hang the device, and is constructed inexpensively to be of a disposable nature.

19 Claims, 2 Drawing Sheets

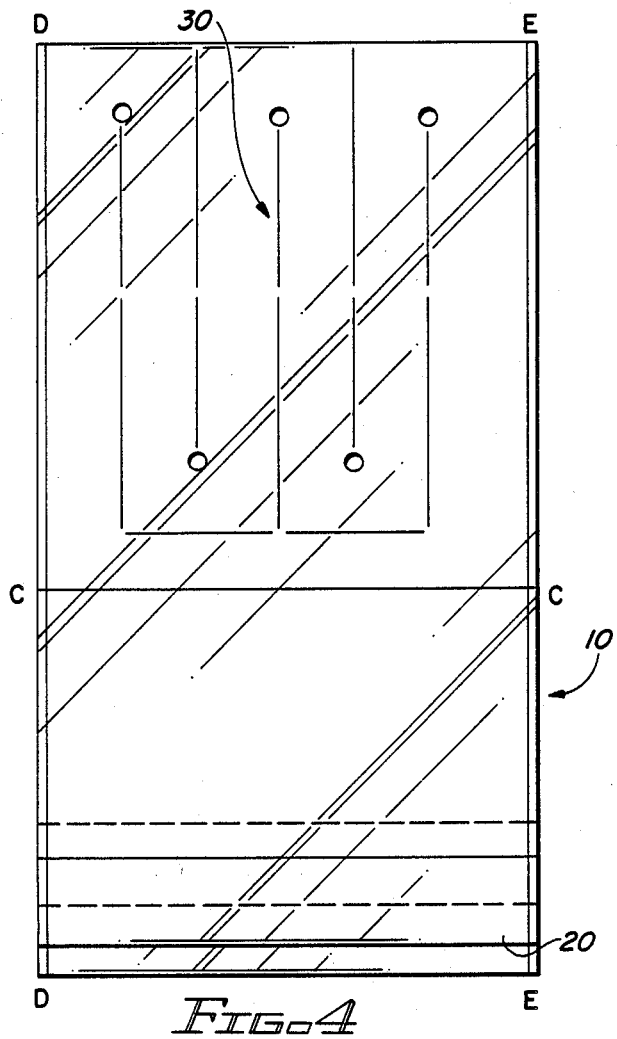
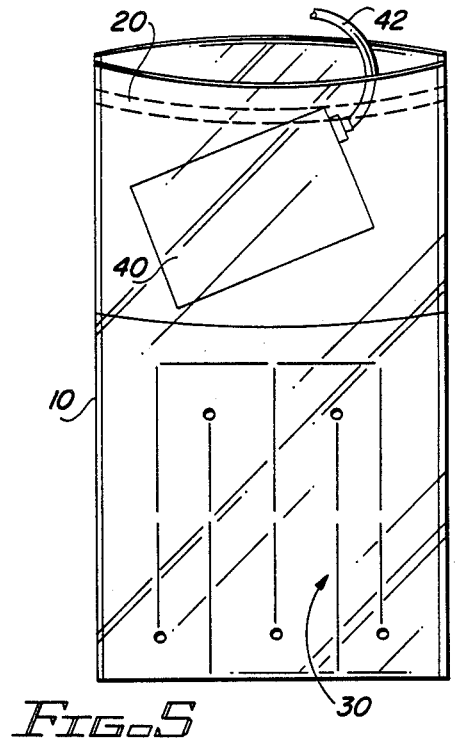
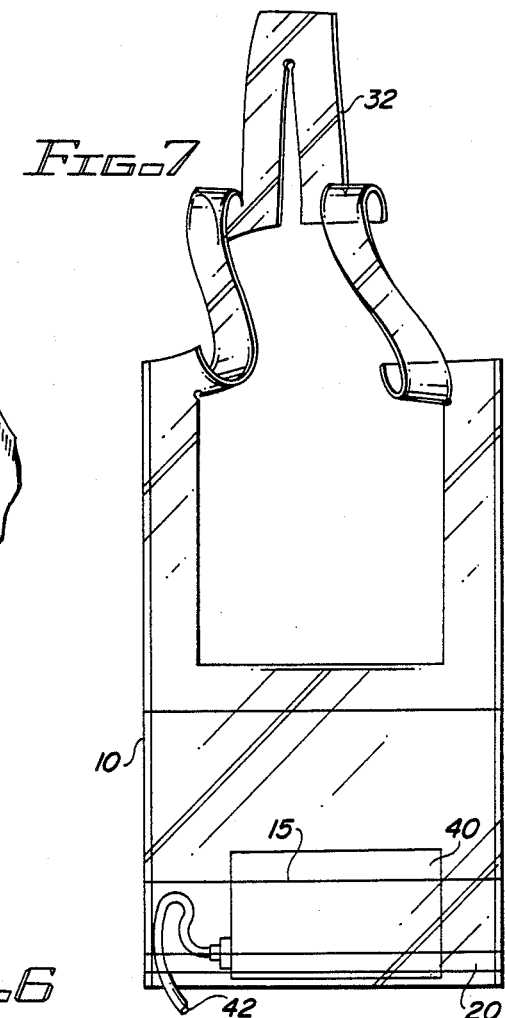

PROTECTIVE BAG FOR WATER-SENSITIVE MEDICAL OR ELECTRONIC APPARATUS

BACKGROUND OF THE INVENTION

1. Field of the Invention

The present invention relates generally to a protective enclosure in which portable medical or other electronic equipment which could be damaged by exposure to water may be temporarily stored and carried by the equipment user, and more particularly to an inexpensive, disposable plastic bag into which a portable miniature medication infusion pump or similar article may be placed for a high degree of water-resistant protection when the user is showering or is outside in the rain, the bag having a strap for wearing of the bag by the user.

An alternative technique to multiple daily injections of insulin for insulin-dependent diabetics is the use of a miniature electronically-controlled infusion pump to provide a large number of small doses of insulin around the clock. Such infusion pumps are typically the size of a pack of cigarettes or smaller, and supply insulin to the user through a small infusion set having a fine needle designed for use with the infusion pump.

It may be appreciated that since insulin is delivered in a large number of small doses (typically one dose is provided every three to twelve minutes), it is desirable to have the infusion pump connected and operating continuously. It is therefore undesirable for the user to disconnect the infusion pump other than to change infusion sets or to refill the infusion pump.

One of the problems faced by most users of portable infusion pumps is the difficulty of bathing or showering while wearing the infusion pump. Since most infusion pumps are not waterproof, or even highly water-resistant, it is not possible to wear the infusion pump into the shower. The user is then faced with the undesirable alternative of either not showering but rather using an alternative bathing technique such as a sponge bath, or removing the infusion pump and infusion set to shower, a process involving shutting down the pump temporarily while showering and installing a new infusion set and restarting the infusion pump after showering.

Most users of infusion set dislike having to install infusion sets more often than absolutely necessary. To install a new infusion set (which is generally recommended after removing an infusion set for showering), the new set must first be connected to the infusion pump and primed. Following this operation, the new infusion set is located and inserted in its subcutaneous location by the user. It may be appreciated that for most users of insulin infusion pumps, it would be desirable to avoid the time-consuming and inconvenient necessity of removing the infusion pump while showering.

Similarly, users of infusion pumps must also exercise precaution when outdoors during rainy weather, since exposure of the infusion pump to rain may cause damage to the pump. When outdoors it is sometimes difficult to avoid entirely a situation where there is a possibility of encountering rain. While such an occurrence will cause only inconvenience to nonusers of a pump, for wearers of an infusion pump the damages may be substantial, including damage causing the pump to cease operations or to operate in a faulty manner. It may therefore be appreciated that the wearing of an infusion pump presents problems to the user of the device.

It should also be noted that other electronic devices used outdoors also present the similar problem of water damage in the event of exposure to rain. Examples of such devices include the popular personal tape players and radios, and small cameras.

Potential solutions to the problem must attain certain objects in order to represent true solutions to the aforementioned problems. First and foremost, a solution must represent a convenient way to protect an infusion pump used in a shower environment. The pump must be completely protected, while allowing the continued connection of the infusion set leading from the pump to the user. The solution must be easy to use, and inexpensive to purchase.

The solution must also facilitate protection of the device from a source of falling water such as that encountered in a shower of in a rainfall. Protection on the top side is thereby more critical, and any device opening on the top side thereof would most likely be unacceptable. Since critical display information is presented on a visual display in most infusion pumps, it is necessary that the solution be see-through at least in part to allow inspection of the display by the user even while the pump is being protected from the wet environment.

The protection must also be secure, since a failure of the protection would not only place the infusion pump in the wet environment, but could also subject the pump to a sharp impact if the pump falls to the floor (which fall would also be likely to rip out the infusion set in a painful manner). Finally, it is desirable that the protection be as inexpensive as possible, to thereby encourage purchase and use by pump wearers, as well as to enable the successful production and marketing of a substantial number of protection devices.

SUMMARY OF THE INVENTION

The disadvantages and limitations of the background art discussed above are overcome by the present invention. With this invention, a disposable one-use plastic bag is used to securely store an infusion pump or similar electronic device from a wet environment. The bag opens at the bottom thereof to facilitate insertion of the infusion pump into the bag, and closes securely with an adhesive strip located on an interior-facing surface of the bag, leaving the infusion set extending from the bottom of the bag.

An inner pouch fully supports the infusion pump within the bag, thereby preventing a distribution of the weight of the pump on the adhesive seal closing the entrance to the bag. The inner pouch also enhances the water-resistance of the bag, since water would have to move upwards past the adhesive seal and over the edge of the inner pouch to reach the infusion pump. The bag may easily be constructed of clear plastic material, thereby allowing easy viewing of the infusion pump display through the sides of the bag.

The bag is also manufactured with a perforated portion which may be easily opened up to form a strap by which the bag may be carried in an upright position maximizing water protection of the infusion pump contained within the bag. The strap may be worn on the shoulder or around the neck of the user, or it may be used to hang the bag from a hook of even the showerhead within the shower, thereby freeing the user to shower. Best of all, the bag is easy and convenient to use, and may be opened and closed quickly with a minimum of effort by the user, while not in the least compromising the high degree of protection afforded against water damage to the infusion pump contained within the bag.

It may therefore be seen that the present invention teaches an inexpensive device which affords excellent protection to an infusion pump or other similar electronic device against water damage in a shower or rain type of environment, while supporting the pump in a highly safe and secure manner. The device is disposable, and is easily used to protect the infusion pump. The see through construction of the device allows the user to monitor the operation of the infusion pump, and the integral strap enables the bag and the pump to be conveniently supported in a position affording maximum protection to the pump. Most importantly, the present invention finally provides a desirable alternative to users of insulin infusion pumps which allows them to freely shower in a convenient and normal way.

DESCRIPTION OF THE DRAWINGS

These and other advantages of the present invention are best understood with reference to the drawings, in which:

FIG. 4 is a plan view of the completed bag showing the sealed seams on the sides of the bag and the perforations forming the strap of the bag;

FIG. 5 illustrates how an infusion pump is initially installed into the bag through the bottom of the bag while the bag is inverted;

FIG. 6 shows how the adhesive seal is closed by the hands of a user of the bag;

FIG. 7 shows how the pump drops into the inner pouch of the bag, as well as how the strap is opened up;

DETAILED DESCRIPTION OF THE PREFERRED EMBODIMENT

The preferred embodiment of the present invention is illustrated in various stages of construction in FIGS. 1 through 4. A bag 10 is manufactured from a rectangular sheet 12 of thin, flexible material shown best in FIG. 1, which material in the preferred embodiment is a clear plastic such as polyethylene, ethylene-vinyl acetate (EVA), or polypropylene. The sheet 12 is of a width sufficient to easily accommodate the portable miniature infusion pump (FIGS. 5-7) or other device to be secured within the bag 10. Typically, the sheet 12 is approximately 4-8 inches wide. The sheet 12 of thin material will be folded across two major fold lines extending across the narrow width of the sheet 12, the first being line A—A near the bottom of the sheet 12 and the second being line B—B above the middle of the sheet 12.

Figure 1:
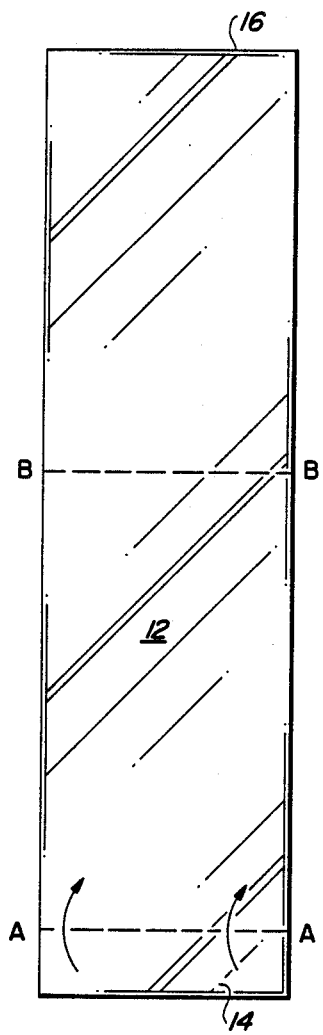
FIG. 1 is a plan view of a flat plastic sheet from which the present invention is constructed illustrating the first fold made in that construction.
Figure 2:
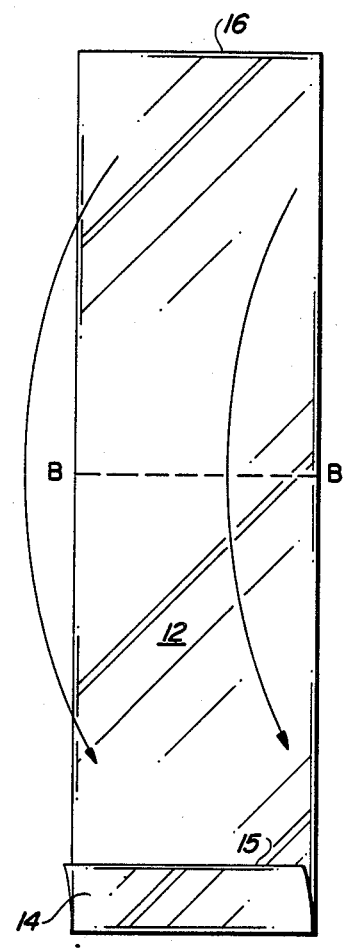
FIG. 2 is a plan view of the plastic sheet of FIG. 1 showing the first fold made, and further illustrating the second fold made in construction of the device.

The portion of the sheet 12 below line A—A is a flap 14, which flap 14 is folded across the line A—A shown in FIG. 1 against the sheet 12, as shown in FIG. 2. By folding the top edge of the flap 14 against the sheet 12, a pouch 18 (best shown in FIG. 3) is created therebetween. The flap 14 is of a height sufficient to protect a pump (FIGS. 5-7) or other device contained in the pouch 18 by preventing water entering over the top edge 15 of the flap 14 and into the pouch 18. Typically, the flap 14 is 1-4 inches high.

Figure 3:
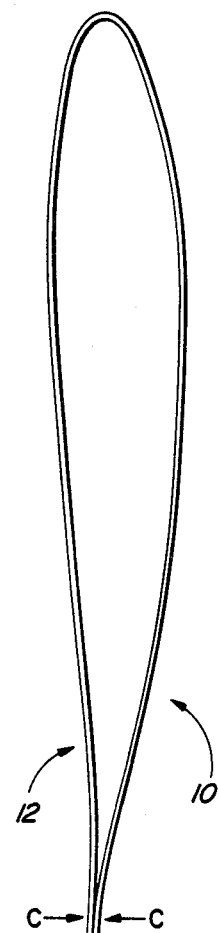
FIG. 3 is a side view of the plastic sheet of FIGS. 1 and 2 following completion of the first and second folds, and also showing the sealed seam between the enclosure portion of the bag and the strap portion of the bag, the construction of the preferred adhesive seal for the bag, and the inner pouch of the bag.

The other edge 16 of the sheet 12, which is on the end of the sheet 12 away from the flap 14, is then folded down across line B—B of FIG. 2, to form the folded shape bag 10 illustrated in FIG. 3. When folded, the edge 16 of the sheet 12 preferably extends nearly to the bottom of the pouch 18 formed in the folded shape bag 10, as shown in FIG. 3, although it is certainly possible for the edge 16 of the sheet 12 to extend beyond the bottom of the pouch 18. It is necessary for the edge 16 of the sheet 12 to extend well past the top edge 15 of the flap 14 to provide a water-resistant closure for the pouch 18.

The pouch 18, which as thus far described is bounded by the fold A—A (FIG. 1) on the bottom, is bounded on the top by a seam C—C formed between the portion of the sheet 12 between folds A—A and B—B and the portion of the sheet 12 folded over across line B—B. It is preferable that the pouch 18 extend sufficiently above the top edge 15 of the flap 14 toward the seam C—C to allow the pump (shown in FIGS. 5-7) or other device to be inserted into the pouch 18 from between the edge 16 of the sheet 12 and the top edge 15 of the flap 14. Such a pouch 18 would, for example, be approximately 2-8 inches high.

The seam C—C extends across the width of the bag 12, and thereby below the seam C—C defines the pouch 18 and above the seam C—C defines the portion of the bag 12 which will be made into a strap (to be discussed more fully below). The seam C—C is preferable a heat-sealed seam, the making of which is well known in the art. Instead of a heat-sealed seam, however, an adhesive seam or an ultrasonic seam could also be utilized. The only limitation is that the seam C—C must be both durable and waterproof.

At this time, the adhesive means to seal the pouch 18 may be installed. In the preferred embodiment shown in FIG. 3, a strip of tape 20 is used to provide the seal. The strip of tape 20 has an adhesive surface 22 along approximately two-thirds of the width thereof. The additional third of the width of the tape 20 does not have an adhesive applied thereto, and is therefore not sticky. Part of the adhesive surface 22 of the tape 20 is secured along the outside surface of the edge 16 of the sheet 12, with a portion of the adhesive surface 22 of the tape 20 extending downwardly over the edge 16 of the sheet 12.

It will therefore be appreciated that a portion of the adhesive surface 22 extends downwardly beyond the edge 16 of the sheet 12, and faces the outside surface of the flap 14 near the bottom thereof. This portion of the adhesive surface 22 is used to secure to pouch 18 in water-resistant fashion. In the process of constructing the bag 10, the portion of the adhesive surface 22 extending beyond the end 16 is fastened to the flap 14, and the bag 10 will be essentially flat. It should be noted that the tape 20 may have more or less than two-thirds of its width coated with the adhesive surface 22, since the two-thirds figure is used as an example only.

Referring now to FIG. 4, two additional seams are formed on the bag 10 of FIG. 4 at the long sides thereof, these seams being seam D—D on one side and seam E—E on the other side. The portions of these seams D—D and E—E below the seam C—C complete the construction of the water-resistant interior of the bag 10, as defined by the pouch 18, and the end 16. The seams D—D and E—E may be made in the same manner as the seam C—C. It may be noted that it is not necessary to extend the seam D—D and E—E above the seam C—C, but that to do so is a manufacturing expedient.

It will be appreciated that the orientation of the bag 10 in operation will be in the orientation shown in FIG. 3, namely with the pouch 18 extending in a downwardly direction. Since water from a showerhead, or from rain, falls essentially downwardly, it is apparent that water will not be permitted into the pouch 18. The bag 10 may not be submersible, but submersion of the bag 10 is neither a design requirement nor a feature necessary to most infusion pump users.

The construction of the bag 10 is completed by perforating or otherwise partially cutting the portion of the bag 10 above the seam C—C, which portion is generally indicated as 30, to facilitate use of this portion 30 of the bag 10 as a strap 32 when the perforated areas are opened. (The strap 32 is shown in FIG. 7 in an opened position). It will be appreciated that since the bag 10 is folded over at the top thereof, the portion 30 is two layers thick.

FIGS. 5-7 illustrate the installation of a portable miniature infusion pump 40 into the bag 10. Referring first to FIG. 5, the portion of the tape 20 not having adhesive 22 thereon may be pulled to open the bag 10, whereupon the end 16 is pulled apart from the flap 14 to provide access to the pouch 18. As shown in FIG. 5, the bag 12 is held upside down to facilitate opening the bag 12. The pump 40 is dropped into the pouch 18 in a sideways position as illustrated. Note that there must be sufficient room inside the bag 10 to allow the pump to fit between the seam C—C (FIGS. 3-4) and the edge 15 of the fold 14, to allow the pump 40 to fit into the pouch 18.

The bag 10 is still held in an inverted position in FIG. 6, and the bag 10 may be closed by pulling on the sides of the bag 10 near the bottom as shown. Note that an infusion set 42 extends from the bag 10, but that the adhesive surface 22 (FIG. 3) of the tape 20 will seal around the infusion set 42. The user will then run his or her fingers along the tape 22 to tightly seal the bag 10.

Referring now to FIG. 7, the bag 10 may be returned to right side up, and the pump 40 will fall into the pouch 18. It is important that the pump 40 fit inside the pouch 18 (inside the flap 14) for proper water resistance. The perforated area 30 may be opened to form the strap 32, which strap 32 is sized as desired to fit around the user's neck (or shoulder), as well as on a hook or over a showerhead. Typically the length of the strap will be 20-45 inches, depending on where the bag 10 is to be worn or installed.

Figure 8:
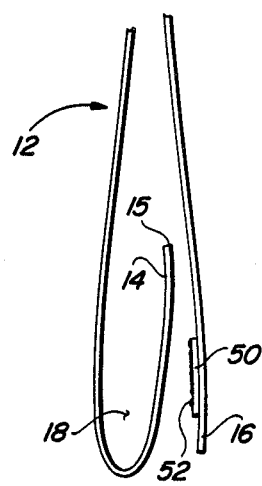
FIG. 8 illustrates a side view analogous to the lower portion of FIG. 3, but showing an alternative embodiment for the adhesive securing the bottom of the bag.
Figure 9:
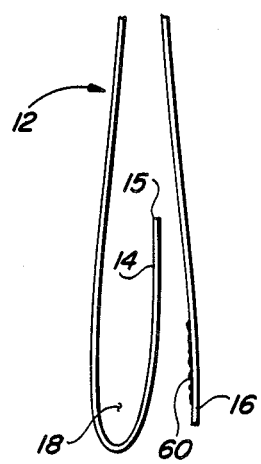
FIG. 9 illustrates an additional side view analogous to the power portion of FIG. 3, showing a second alternate embodiment for the adhesive securing the bottom of the bag.

It will be apparent to those skilled in the art that a variety of design differences may be made in the present invention. Two such differences in the method used to achieve an adhesive seal are illustrated in FIGS. 8 and 9. Referring first to FIG. 8, a length of two sided tape 50 is used instead of the tape 20 shown in FIG. 3. The two sided tape 50 is preferably secured to the side of the edge 16 facing the flap 14 with an adhesive surface facing the flap 14. It would be just as possible to install the tape 50 on the flap instead of on the edge 16.

Similarly, in FIG. 9, an adhesive material 60 is shown applied to the side of the edge 16 facing the flap 14. The adhesive material could also be located on the flap 14 instead of on the edge 16. Another possible modification would be to form all the seams (C—C, D—D, and E—E) before installation of the tape 20. The tape would then be applied to the edge 16 after the bag 10 is otherwise completed. This in no way departs from the present invention.

The bag 10 is preferably made of a clear material to allow the user to monitor the operation of the pump 40 and view any displays thereon (not shown). The tape 20 in FIG. 3 may also be provided with a colored surface in the areas of the tape 20 not treated with the adhesive surface 22. This will indicate to the user where to pull the tape 20 to open the bag 10. Likewise, in the embodiments shown in FIGS. 8 and 9, a colored surface could be provided along the edge 16.

It will be appreciated that the present invention teaches the construction of a protective bag 10 which may be used to safeguard an infusion pump 40 from water in a shower or in the rain (or just as easily to protect other water sensitive electronic devices, including portable radios, tape players, and cameras). The pouch 18 is secure, and since the pump 40 is within the pouch 18 on the inside of the flap 14, no strain is put on the tape 20 which might inadvertently open the bag 10.

The bag 10 may be economically constructed, and of a disposable nature. A display on the pump 40 in the bag 10 may be seen through the bag 10 if it is constructed of clear material. The water resistance of the bag 10 of the present invention is quite good, and the bag 10 thus presents substantial advantage without presenting any relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A protective, water-resistant bag for temporarily storing a small medical or electronic apparatus which apparatus is sensitive to water damage, said apparatus being connected to a tube or cord leading from said apparatus to the user of said apparatus, said bag comprising:

a pouch formed by a first segment of thin material having a flap attached to the bottom edge thereof and folded upward therefrom, said flap not extending to the top edge of said first segment of thin material, said apparatus being stored in said pouch prior to entry into a wet environment;

a second segment of thin material sealingly attached at the top edge thereof to said top edge of said first segment of thin material, said second segment of thin material extending downwardly over at least a portion of said flap, the sides of said first and second segments of thin material being sealingly attached together, thereby sealing said pouch save for an opening between said second segment and said flap and shielding said apparatus from a wet environment, said tube or cord extending from said apparatus in said pouch over said flap and between said flap and said second segment of thin material, said tube or cord thereby extending out of said bag;

adhesive sealing means for removably sealing said second segment of thin material to said flap around a portion of said tube or cord located between said flap and said second segment of thin material, thereby making said pouch water-resistant; and means for supporting said pouch and said first and second segments of thin material, said supporting means being attached to the top edges of said first and second segments of thin material.

2. A bag as defined in claim 1, wherein the material used for the manufacture of said first and second segments of thin material is transparent to allow said apparatus to be viewed through said pouch.

3. A bag as defined in claim 1, wherein the material used for the manufacture of said first and second segments of thin material is one of the materials from the group consisting of polyethylene, ethylene-vinyl acetate, or polypropylene.

4. A bag as defined in claim 1, wherein said flap and said first and second segments of thin material are all portions of a single piece of thin material.

5. A bag as defined in claim 1, wherein said flap is sufficiently spaced away from said top edge of said first segment of thin material to allow said apparatus to be inserted into and removed from said pouch.

6. A bag as defined in claim 5, wherein said flap is approximately 1-4 inches high and said pouch is 2-8 inches high.

7. A bag as defined in claim 1, wherein said second segment of thin material is heat sealed at the top and side edges thereof to said first segment of thin material at the top and side edges thereof.

8. A bag as defined in claim 1, additionally comprising:

a third segment of thin material forming a loop, one end of which loop is attached to said top edge of said first segment of thin material, the other end of which loop is attached to said top edge of said second segment of thin material, said loop extending in a direction essentially opposite to said pouch.

9. A bag as defined in claim 8, wherein said supporting means comprises:

perforations in said loop defining a strap, said perforations when broken open causing said loop to form said strap, which may be used to support said pouch.

10. A bag as defined in claim 8, wherein said flap, said loop, and said first and second segments are all adjacent portions of a single rectangular piece of material, with said flap being on one end of said piece of material, said first segment being located between said flap and said one end of said loop, said other end of said loop being adjacent said second segment of said thin material, and said second segment of said thin material being the other end of said piece of material.

11. A bag as defined in claim 1, wherein said sealing means comprises:

a strip of tape having an adhesive surface on one side thereof, with a first portion of said one side of said strip of tape along one edge of said strip of tape having no adhesive surface thereon, the balance of said one side of said strip of tape being a second portion with an adhesive surface thereon, the other edge of said strip of tape which comprises part but not all of said second portion being secured to said second segment of thin material in a manner whereby said strip of tape extends from the edge of said second segment nearest the bottom of said flap, the part of said second portion not secured to said second segment and having adhesive thereon being used to removeably seal said pouch by pressing said part of said second portion not secured to said second segment against said flap.

12. A bag as defined in claim 11, wherein said tape has a colored portion used to indicate the edge which may be pulled to open said pouch.

13. A bag as defined in claim 1, wherein said sealing means comprises:

a strip of tape having an adhesive surface on both sides thereof, said strip of tape being secured on one side to one of the side of said second segment of thin material facing said flap or said flap at a location where it faces said second segment, said pouch being sealed by pressing the other side of said strip of tape against the other of the side of said second segment of thin material facing said flap or said flap at a location where it faces said second segment.

14. A bag as defined in claim 1, wherein said sealing means comprises:

an adhesive surface on one of the side of said second segment of thin material facing said flap or said flap at a location where it faces said second segment, said pouch being sealed by pressing said adhesive surface against the other of the side of said second segment of thin material facing said flap or said flap at a location where it faces said second segment.

15. A water-resistant bag for temporarily storing a small medical or electronic apparatus which apparatus is sensitive to water damage, said apparatus being connected to a tube or cord leading from said apparatus to the user of said apparatus, said bag comprising:

a rectangular sheet of thin, flexible material having a top edge and a bottom edge, and two side edges, said sheet having a flap including said bottom edge which is folded up in a first fold, said sheet also having said top edge folded down in a second fold to a location near to the bottom of said flap;

a first seam formed by sealing together across the width of said sheet a portion of said sheet located between the two folds and a portion of said sheet between said second fold and said top edge, thereby forming below said first seam a pouch between said first seam and said first fold, and also thereby forming a loop of material above said first seam, said apparatus being stored in said pouch prior to entry into a wet environment;

second and third seams sealing said two sides of said sheet to enclose said pouch and shield said apparatus from a wet environment, said tube or cord extending from said apparatus in said pouch over said flap and between said flap and the portion of said sheet adjacent said top edge, said tube or cord thereby extending out of said bag;

adhesive sealing means provided on said portion of said sheet adjacent said top edge to removably seal said portion of said sheet adjacent said top edge to said flap around a portion of said tube or cord located between said flap and said portion of said sheet adjacent said top edge, thereby making said pouch water-resistant; and means, including said loop, for supporting said pouch around the neck of a user of said bag.

16. A bag as defined in claim 15, further comprising means for indicating the appropriate location to open said bag.

17. A protective, water-resistant bag for temporarily storing a small medical or electronic apparatus which apparatus is sensitive to water damage, said apparatus being connected to a tube or cord leading from said apparatus to the user of said apparatus, said bag comprising:

a rectangular sheet of thin, flexible material having a top edge and a bottom edge, and two side edges, said sheet having a first portion thereof including said bottom edge, a second portion thereof including said top edge, and a third portion hereof interposed between said first and second portions, said first portion defining a flap which flap is folded up from said third portion in a first fold, said second portion folded down in a second fold from said third portion bringing said top edge to a location near to the portion of said flap adjacent said first fold;

a first seam formed by sealing together across the width of said sheet a segment of said second portion intermediate said second fold and said top edge to a segment of said third portion intermediate said first and second folds and above said flap, thereby forming below said first seam a pouch located between said first seam and said first fold and defined by said first portion of said sheet and the parts of said second and third portions of said sheet below said first seam, and also thereby forming a loop of material above said first seam and defined by the parts of said second and third portions of said sheet above said first seam, said apparatus being stored in said pouch prior to entry into a wet environment;

second and third seams sealing said two sides of said sheet to enclose said pouch and shield said apparatus from a wet environment, said tube or cord extending from said apparatus in said pouch over said flap and between said flap and the part of said second portion adjacent said top edge, said tube or cord thereby extending out of said bag;

adhesive sealing means provided on said portion of said sheet adjacent said top edge to removably seal said portion of said sheet adjacent said top edge to said flap around a portion of said tube or cord located between said flap and said part of said second portion adjacent said top edge, thereby making said pouch water-resistant; and perforations in the parts of said second and third portions of said sheet above said first seam defining a strap, said perforations when broken open causing said parts of said second and third portions of said sheet above said first seam to form said strap, which may be used to support said pouch.

18. A method of making a protective, water-resistant bag for temporarily storing a small medical or electronic apparatus which apparatus is sensitive to water damage, said apparatus being connected to a tube or cord leading from said apparatus to the user of said apparatus, said method comprising:

providing a pouch formed by a first segment of thin material having a flap attached to the bottom edge thereof and folded upward therefrom, said flap not extending to the top edge of said first segment of thin material, said apparatus being stored in said pouch prior to entry into a wet environment;

attaching a second segment of thin material at the top edge thereof in a sealing fashion to said top edge of said first segment of thin material, said second segment extending downwardly over at least a portion of said flap;

sealing the sides of said first and second segments of thin material together, thereby sealing said pouch save for an opening between said second segment and said flap and shielding said apparatus from a wet environment, said tube or cord extending from said apparatus in said pouch over said flap and between said flap and said second segment, said tube or cord thereby extending out of said bag;

providing adhesive sealing means on said second segment to removeably seal said second segment to said flap around a portion of said tube or cord located between said flap and said segment, thereby making said pouch water-resistant; and supporting said pouch and said segment at the top of said sheet of thin material.

19. A method of making a protective, water-resistant bag for temporarily storing a small medical or electronic apparatus which apparatus is sensitive to water damage, said apparatus being connected to a tube or cord leading from said apparatus to the user of said apparatus, said method comprising:

providing a rectangular sheet of thin, flexible material having a top edge and a bottom edge, and two side edges;

folding a flap of said sheet including said bottom edge up to form a first fold;

folding said sheet to bring said top edge down to a location near to the bottom of said flap to form a second fold;

sealing together across the width of said sheet to form a first seam between a portion of said sheet located between the two folds and above said flap, and a portion of said sheet between said second fold and said top edge, thereby forming below said first seam a pouch between said first seam and said first fold, which pouch is covered by the portion of said sheet between said first seam and said top edge, said apparatus being stored in said pouch prior to entry into a wet environment;

sealing the sides of said sheet to enclose said pouch and shield said apparatus from a wet environment, said tube or cord extending from said apparatus in said pouch over said flap and between said flap and the portion of said sheet adjacent the said top edge, said tube or cord thereby extending out of said bag;

providing adhesive sealing means on said top edge to removeably seal said top edge to said flap around a portion of said tube or cord located between said flap and said segment, thereby making said pouch water-resistant; and providing in the portion of said sheet above said first seam means for supporting said pouch around the neck of a user of said enclosure.

* * * * *